United States Patent
Song

(10) Patent No.: US 9,884,800 B2
(45) Date of Patent: Feb. 6, 2018

(54) METHOD OF PREPARING 1,3-BUTADIENE AND METHYL ETHYL KETONE FROM 2,3-BUTANEDIOL USING ADIABATIC REACTOR

(71) Applicant: SK INNOVATION CO., LTD., Seoul (KR)

(72) Inventor: Dae Sung Song, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 0 days.

(21) Appl. No.: 15/477,618

(22) Filed: Apr. 3, 2017

(65) Prior Publication Data

US 2017/0342009 A1 Nov. 30, 2017

(30) Foreign Application Priority Data

May 24, 2016 (KR) .................. 10-2016-0063681

(51) Int. Cl.
    *C07C 45/45* (2006.01)
    *C07C 1/24* (2006.01)
(52) U.S. Cl.
    CPC ............... *C07C 45/45* (2013.01); *C07C 1/24* (2013.01); *C07C 2527/167* (2013.01)
(58) Field of Classification Search
    CPC .................................. C07C 45/45; C07C 1/24
    USPC ........................................................ 568/405
    See application file for complete search history.

(56) References Cited

U.S. PATENT DOCUMENTS

| 1,934,055 A | 12/1934 | Carter |
| 2,386,324 A | 10/1945 | Lorch |
| 2016/0122264 A1 | 5/2016 | Olbert et al. |

FOREIGN PATENT DOCUMENTS

| KR | 1020120096125 | 8/2012 |
| KR | 102012009818 | 9/2012 |
| KR | 101298672 | 8/2013 |
| WO | 2009151342 A1 | 12/2009 |
| WO | 2014202501 A1 | 12/2014 |

*Primary Examiner* — Sikarl Witherspoon
(74) *Attorney, Agent, or Firm* — Abelman, Frayne & Schwab

(57) ABSTRACT

Disclosed is a method of preparing 1,3-butadiene and methyl ethyl ketone from 2,3-butanediol, including: a) providing a plurality of adiabatic reactors, which include a catalyst bed for dehydrating 2,3-butanediol, without a heat transfer medium, and are connected in series; b) introducing a stream including 2,3-butanediol at a temperature ranging from 200° C. to 400° C. into a first adiabatic reactor among the plurality of adiabatic reactors; c) dehydrating the 2,3-butanediol so as to be converted into 1,3-butadiene and methyl ethyl ketone and discharging a product stream including 1,3-butadiene and methyl ethyl ketone; d) heating the discharged product stream to to 200° C. to 400° C.; and e) introducing the heated product stream into a second adiabatic reactor so that 2,3-butanediol is further dehydrated and converted into 1,3-butadiene and methyl ethyl ketone and then discharging the product stream including 1,3-butadiene and methyl ethyl ketone.

9 Claims, 1 Drawing Sheet

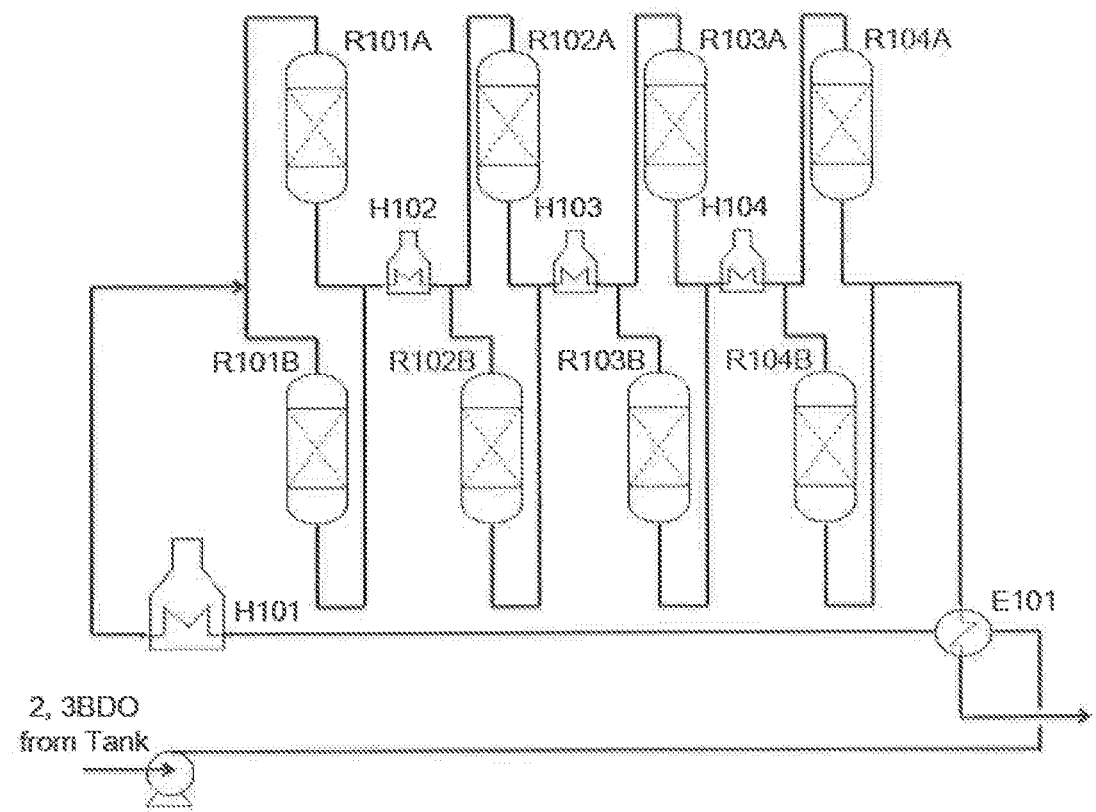

METHOD OF PREPARING 1,3-BUTADIENE AND METHYL ETHYL KETONE FROM 2,3-BUTANEDIOL USING ADIABATIC REACTOR

CROSS-REFERENCE TO RELATED APPLICATION

This application claims the benefit of Korean Patent Application No. 10-2016-0063681, filed May 24, 2016, entitled "Method for preparing 1,3-butadiene and methylethylketone from 2,3-butanediol using an adiabatic reactor", which is hereby incorporated by reference in its entirety into this application.

BACKGROUND OF THE DISCLOSURE

1. Technical Field

The present disclosure relates to a method of preparing 1,3-butadiene and methyl ethyl ketone from 2,3-butanediol using an adiabatic reactor.

2. Description of the Related Art 1,3-butadiene is widely utilized as a material for synthetic rubber for use in car tires. When styrene is polymerized with acrylonitrile, synthetic rubber products such as ABS (acrylonitrile-butadiene-styrene), NBR (acrylonitrile-butadiene rubber) and SBR (styrene-butadiene rubber) are obtained.

1,3-butadiene is prepared as a byproduct during steam cracking of crude oil to obtain ethylene and olefin. Also, it may be produced through oxidative dehydrogenation of n-butane or butene. In the United States and the former Soviet Union in the past, an alcohol produced from cereal was simultaneously dehydrogenated and condensed in the presence of a metal oxide catalyst, and was thus converted into 1,3-butadiene.

In particular, techniques for preparing 1,3-butadiene were actively studied by IG Farben of Germany during World War II, and the preparation of 1,3-butadiene by IG Farben is a process in which acetylene derived from coal is converted into acetaldehyde or acetol to give 1,3-butanediol, which is then reacted in the presence of an acid or base catalyst and thus converted into 1,3-butadiene.

U.S. Pat. No. 1,984,055 discloses the conversion of 1,3-butanediol into 1,3-butadiene using catalysts such as sodium hydrogen phosphate, calcium-ammonium phosphate and sodium n-butylamine phosphate. These catalysts are reported to exhibit 1,3-butadiene selectivity of at least 85% and superior durability.

Also, U.S. Pat. No. 2,386,324 discloses the conversion of a 1,3-butanediol aqueous solution into 1,3-butadiene using a diammonium phosphate catalyst, in which a yield of 50% was confirmed through evaluation for 56 days.

Meanwhile, methyl ethyl ketone (MEK) is produced from 2-butanol through dehydrogenation using a catalyst such as Cu, Zn or the like, and may be obtained through a liquid-phase oxidation reaction of a carbon compound resulting from a Fischer-Tropsch process or Heavy Naphtha processing.

Recently known are techniques for preparing 1,3-butadiene from 2,3-butanediol obtained through fermentation in addition to intermediate products obtained through petrochemical processing. In this regard, WO 2009151342 discloses a process of producing 2,3-butanediol from syngas through microbial fermentation, and the produced 2,3-butanediol may be converted into 1,3-butadiene and methyl ethyl ketone in the presence of a catalyst.

Korean Patent Application Publication No. 10-2012-0099818 discloses the preparation of 1,3-butadiene and methyl ethyl ketone, the sum of the selectivities of which is 95% at a reaction temperature of 400° C. to 500° C. using a cesium oxide-silica catalyst.

Korean Patent No. 10-1287167 discloses the preparation of a calcium phosphate catalyst having a hydroxyapatite (HAP) structure, a calcium pyrophosphate structure and mixtures thereof. These catalysts are individual calcium phosphate compounds having structural formulas of $Ca_5(PO_4)_3OH$ and $Ca_2(P_2O_7)$ and show specific crystalline structures. These catalysts are thermally treated in a temperature range of 300° C. to 700° C. and applied under conditions of a reaction temperature of 380° C. and 2 atm, whereby 25.2% of 1,3-butadiene is produced when methyl ethyl ketone is produced at a maximum of 64.5%, and methyl ethyl ketone is obtained at a maximum of 50.4% when 1,3-butadiene is produced at a maximum of 37.4%.

Korean Patent No. 10-1298672 discloses the preparation of 1,3-butadiene, the selectivity of which is 61% through reaction at 360° C. by adding HAP with alumina in order to increase the selectivity of 1,3-butadiene.

These patents pertain to a calcium phosphate catalyst having a HAP structure or a calcium pyrophosphate structure, among calcium phosphate catalysts.

The dehydration reaction of 2,3-butanediol is highly endothermic, and thus the temperature of the reactor is lowered as the reaction progresses. Thus, maintaining the temperature at which 2,3-butanediol may be maximally converted into 1,3-butadiene is regarded as important.

Korean Patent Application Publication No. 10-2016-0021821 discloses a shell-and-tube reactor, which is not used in the dehydration of 2,3-butanediol, but is a reactor capable of being maintained at a constant temperature. The shell-and-tube reactor is configured such that multiple tubes are filled with a catalyst, and the outside of the tubes is heated by means of a heat transfer medium, thereby constantly maintaining the temperature of the reactor. However, the shell-and-tube reactor has to use a heat transfer medium that is sable at high temperatures (e.g. a molten salt) and is thus expensive and needs additional devices, and the maintenance thereof is difficult.

SUMMARY OF THE DISCLOSURE

Accordingly, the present disclosure has been made keeping in mind the problems encountered in the related art, resulting in the finding that, when 1,3-butadiene and methyl ethyl ketone are prepared from 2,3-butanediol using an adiabatic reactor that obviates a heat transfer medium, 2,3-butanediol may be economically and efficiently converted into 1,3-butadiene and methyl ethyl ketone, thus culminating in the present disclosure.

Accordingly, an aspect of the present disclosure is intended to provide a method of preparing 1,3-butadiene and methyl ethyl ketone from 2,3-butanediol using an adiabatic reactor.

In order to accomplish the above aspect, an embodiment of the present disclosure provides a method of preparing 1,3-butadiene and methyl ethyl ketone from 2,3-butanediol using an adiabatic reactor, comprising: a) providing a plurality of adiabatic reactors, which include a catalyst bed for dehydrating 2,3-butanediol, without a heat transfer medium, and are connected in series; b) introducing a stream including 2,3-butanediol at a temperature ranging from 200° C. to 400° C. into a first adiabatic reactor among the plurality of adiabatic reactors; c) dehydrating the 2,3-butanediol so as to be converted into 1,3-butadiene and methyl ethyl ketone and discharging a product stream including 1,3-butadiene and methyl ethyl ketone; d) heating the discharged product stream to 200° C. to 400° C.; and e) introducing the heated product stream into a second adiabatic reactor so that 2,3-butanediol is further dehydrated and converted into 1,3-butadiene and methyl ethyl ketone and then discharging the product stream including 1,3-butadiene and methyl ethyl ketone.

This method may further comprise f) heating the product stream, discharged from the second adiabatic reactor, to 200° C. to 400° C. and sequentially introducing the product stream into a subsequent adiabatic reactor.

In an exemplary embodiment, when a conversion of 2,3-butanediol in the product stream is 99.9% or more, the product stream is not supplied into the subsequent adiabatic reactor but may be obtained as a final product stream.

In an exemplary embodiment, when a molar concentration of 3-buten-2-ol (3B2OL) in the product stream is 0.1% or less, the product stream is not supplied into the subsequent adiabatic reactor but may be obtained as a final product stream.

In an exemplary embodiment, the heating the discharged product stream in d) may be performed in a manner in which a temperature of the product stream is increased by 10° C. to 150° C.

In an exemplary embodiment, the catalyst for dehydrating may be an amorphous calcium phosphate-based catalyst.

In an exemplary embodiment, a Ca/P molar ratio of the amorphous calcium phosphate-based catalyst may range from 1.20 to 1.67.

In an exemplary embodiment, a pressure of the stream introduced into the adiabatic reactor may range from 0.1 kgf/cm² g to 6 kgf/cm² g.

In an exemplary embodiment, a weight hourly space velocity (WHSV) of the stream introduced into the adiabatic reactor may range from 0.1 hr$^{-1}$ to 4.8 hr$^{-1}$.

According to an embodiment of the present disclosure, 2,3-butanediol can be economically and efficiently converted into 1,3-butadiene and methyl ethyl ketone using an inexpensive adiabatic reactor that obviates a heat transfer medium.

BRIEF DESCRIPTION OF THE DRAWING

FIG. 1 schematically shows a process of preparing 1,3-butadiene and methyl ethyl ketone from 2,3-butanediol according to an embodiment.

DESCRIPTION OF SPECIFIC EMBODIMENTS

Before the present disclosure is described in more detail, it must be noted that the terms and words used in the present specification and claims should not be interpreted as being limited to typical meanings or dictionary definitions, but should be interpreted as having meanings and concepts relevant to the technical scope of the present disclosure based on the rule according to which an inventor can appropriately define a concept implied by a term to best describe the method he or she knows for carrying out the disclosure. Further, the embodiments of the present disclosure are merely illustrative, and are not intended to represent all of the technical ideas of the present disclosure, and thus a variety of equivalents and modifications able to substitute therefor may be provided at the point of time of filing of the present disclosure.

Hereinafter, a detailed description will be given of embodiments of the present disclosure so that the present disclosure may be easily performed by those skilled in the art. In the following description, it is to be noted that a detailed description of the related art, when it would make the gist of the present disclosure unclear, will be omitted.

<2,3-Butanediol (BDO)>

According to an embodiment, 2,3-butanediol is used as a starting material. 2,3-butanediol has four carbon chains and two reaction sites, and is known to be a compound useful in the synthesis of fine chemicals. 2,3-butanediol is called 2,3-butylene glycol, dimethylene glycol, 2,3-dihydroxybutane, or butan-2,3-diol, and has a boiling point of about 177° C. In this specification, 2,3-butanediol is represented by Chemical Formula I below, including all stereoisomers such as (R,R), (S,S) and meso forms, and racemic isomers, partial optical isomers and highly pure optical isomers.

[Chemical Formula 1]

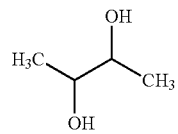

In the present disclosure, 2,3-butanediol, derived from various supply sources through diverse processes without being limited to specific supply sources, may be used as a starting material. According to a specific embodiment, 2,3-butanediol may be typically prepared through fermentation. Examples of bacteria stains useful therein may include *Klebsiella pneumoniae, Bacillus polymyxa, Enterobacter aerogenes, Bacillus subtilis, Aeromonas hydrophilia, Serriatia* spp., etc., and biomass may be used as a carbon source. Recently, a technique for preparing 2,3-butanediol through gas fermentation has become known, and may indicate a biological process for converting CO or $CO_2$ into a low-carbon fuel or chemical.

According to an embodiment, upon gas fermentation for preparing 2,3-butanediol, a carbon monoxide substrate and a fermentation strain, for example, *C. autoethanogenum, C. ljungdahlii, C. ragsdalei*, etc. may be used. The method of preparing 2,3-butanediol through gas fermentation is disclosed in U.S. Patent Application Publication No. 2012/0045807, which is incorporated by reference into the present specification.

<Dehydration of 2,3-butanediol>

According to an embodiment, as shown in Scheme 1 below, 2,3-butanediol is dehydrated in the presence of a catalyst, and is thus converted into 1,3-butadiene and methyl ethyl ketone.

[Scheme 1]

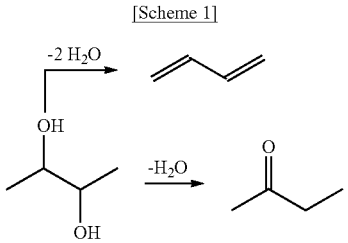

The catalyst for the dehydration of 2,3-butanediol is typically exemplified by an alkaline earth metal phosphate-based catalyst.

In a specific embodiment, the alkaline earth metal phosphate-based catalyst for dehydration, especially a calcium phosphate-based catalyst, may be used. The calcium phosphate-based catalyst may be crystalline or amorphous, and the Ca/P (molar ratio) of the catalyst may range from, for example, about 0.5 to 2.0, particularly about 0.7 to 1.7, and more particularly about 1.0 to 1.67. A more specific example of the catalyst may be a calcium phosphate-based catalyst that is non-crystalline (amorphous) in a Ca/P ratio ranging from about 1.2 to 1.3.

Exemplary properties of the usable calcium phosphate-based catalyst are shown in Table 1 below.

TABLE 1

| Calcium phosphate | Ca/P ratio | pH interval |
|---|---|---|
| Hydroxyapatite ($Ca_{10}(PO_4)_6(OH)_2$) | 1.50-1.67 | >5 |
| Amorphous calcium phosphate | 1.2-1.67 | — |
| Calcium pyrophosphate ($Ca_2P_2O_7$) | About 1.00 | — |

The calcium phosphate-based catalyst has both acid and base properties, and the Ca content of the catalyst is increased as the catalyst is close to the hydroxyapatite structure. As such, relatively strong base properties may result. On the other hand, a catalyst having a calcium pyrophosphate structure shows relatively strong acid intensity. In the case of an amorphous calcium phosphate catalyst having a Ca/P ratio of about 1.2 to 1.3, the amounts of the acid and base are adjusted.

Among the aforementioned catalysts, the calcium phosphate (especially, amorphous calcium phosphate)-based catalyst may be prepared as follows.

Specifically, a phosphoric acid-containing solution is reacted with an alkali component to give an alkali phosphate aqueous solution. As such, the phosphoric acid of the phosphoric acid-containing solution may be at least one selected from among ortho-phosphoric acid ($H_3PO_4$), pyrophosphoric acid ($H_4P_2O_7$), tripolyphosphoric acid ($H_5P_3O_{10}$) and tetrapolyphosphoric acid ($H_6P_4O_{13}$). Particularly useful is phosphoric acid or pyrophosphoric acid, and more particularly useful is pyrophosphoric acid.

In an exemplary embodiment, the alkali component may include a strong base such as NaOH, or a weak base such as ammonia. Particularly useful is a weak base, and more particularly useful is ammonia. When ammonia is used, the amorphous calcium phosphate-based catalyst may be prepared, and the use of the amorphous calcium phosphate-based catalyst may achieve further improved conversion of 2,3-butanediol and selectivity to target compounds (1,3-butadiene and methyl ethyl ketone).

The molar ratio of phosphoric acid/alkali upon the preparation of the alkali phosphate aqueous solution may fall in the range of, for example, about 0.1 to 4, particularly about 0.5 to 2, and more particularly about 1 to 1.67. Also, the pH of the alkali phosphate aqueous solution may fall in the range of, for example, about 4 to 13, particularly about 5 to 11, and more particularly about 6 to 10.

When the alkali phosphate aqueous solution is prepared as described above, a calcium precursor aqueous solution is added to obtain a calcium phosphate slurry. As the calcium precursor, calcium chloride, calcium nitrate, and calcium acetate may be used alone or in combination, and the Ca/P molar ratio may fall in the range of, for example, about 0.5 to 4, particularly about 0.7 to 2, and more particularly about 1 to 1.7.

Thereafter, the calcium phosphate slurry thus prepared is thermally treated, whereby the specific surface area of the phosphate particles is increased through thermal treatment and the activity thereof is also increased. Before thermal treatment, drying the calcium phosphate slurry in the form of a cake may be selectively performed (at, for example, about 50 to 200° C., and particularly about 70 to 150° C.). The exemplary thermal treatment temperature may range from about 300 to 1000° C., particularly about 350 to 800° C., and more particularly about 400 to 700° C. Also, the thermal treatment time may range from, for example, about 1 to 10 hr, particularly about 2 to 8 hr, and more particularly about 4 to 6 hr. In an exemplary embodiment, before or after the thermal treatment process, a molding process may be selectively performed using a molding technique known in the art (e.g. a pellet form).

In an alternative embodiment, examples of the dehydration catalyst may include a solid acid catalyst, such as a zeolite-based catalyst, a silica-alumina catalyst, a zirconia catalyst, a titania catalyst, and a heteropoly acid catalyst.

Examples of the zeolite catalyst may include H-Y, H-BEA, H-ZSM-5, H-MOR, H-MFI, H-FAU, and combinations thereof. The $SiO_2/Al_2O$ molar ratio may range from about 10 to 300, and more particularly about 20 to 50.

The heteropoly acid may be at least one selected from among 12-molybdophosphoric acid ($H_3PMo_{12}O_{40}$), 12-tungstophosphoric acid ($H_3PW_{12}O_{40}$), 12-tungstosiliconic acid ($H_4SiW_{12}O_{40}$), 12-molybdotungstophosphoric acid ($H_3PMo_{12-x}W_xO_{40}$, x=0-12), 12-molybdovanadophosphoric acid ($H_{3+x}PMo_{12-x}V_xO_{40}$, x=0-12), and 12-tungstovanadophosphoric acid ($H_{3+x}PW_{12-x}V_xO_{40}$, x=0-12).

<Dehydration of 2,3-butanediol>

When 2,3-butanediol is dehydrated in the presence of a dehydration catalyst, not only 1,3-butadiene and methyl ethyl ketone, but also light impurities (e.g. 1-butene, 2-butene, etc.), byproducts such as oxygen-containing compounds (e.g. acetaldehyde, 2-MPA (Methyl Propanal), 3-buten-2-ol, 2-butanol, 2-MPO (Methyl Propanol), 3-hydroxy-2-butanon, etc.), heavy components, and a large amount of water are produced. The use of the amorphous calcium phosphate-based catalyst may result in 1,3-butadiene and methyl ethyl ketone (MEK) as main products, 3-buten-2-ol and 2-MPA as main byproducts, and butenes and heavy components as impurities. The expected reaction route, except for the impurities (butenes and heavy components), is as follows.

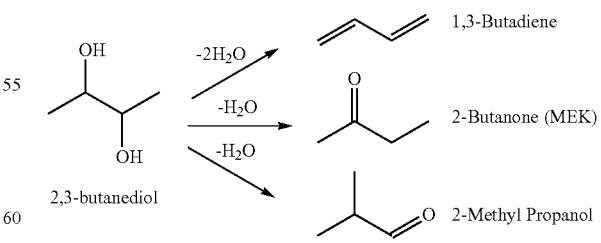

The dehydration of 2,3-butanediol is highly endothermic, and thus, the temperature at which 2,3-butanediol may be maximally converted into 1,3-butadiene has to be maintained constant, which is regarded as important. Hence, the use of a multi-tubular reactor capable of maintaining the internal temperature of the reactor constant is ideal. However, the multi-tubular reactor is expensive and requires additional devices due to the use of a heat transfer medium that is usable at high temperatures (e.g. a molten salt, etc.), and the maintenance thereof is difficult.

In the present disclosure, an adiabatic reactor is used to economically carry out the dehydration of 2,3-butanediol without the need for a heat transfer medium. The adiabatic reactor is a reactor undergoing no heat exchange with the outside. Since heat exchange with the outside is blocked, changes in the temperature of the reaction fluid are caused by the reaction heat. During the endothermic reaction, the internal temperature of the adiabatic reactor is continuously decreased because heat is not supplemented from the outside. Thus, the 2,3-butanediol, serving as the reaction feed, has to reside in the adiabatic reactor in a temperature range suitable for the dehydration.

In order to evaluate the features of the dehydration of 2,3-butanediol, testing was performed under the processing conditions of Table 2 below.

TABLE 2

| | Reactor |
|---|---|
| Kind of reactor | Fixed-bed reactor |
| Size of reactor | Diameter: 3 cm, height; 1.3 m |
| Catalyst | Kind: amorphous calcium phosphate-based catalyst (Ca/P molar ratio: 1.2) |
| | Diameter: 2.85 mm, weight: 80 g |
| | Catalyst loading: loading in a space between 0.6 m from the top of the reactor and 0.3 m from the bottom of the reactor. |
| | (The space up to 0.6 m from the top of the reactor and up to 0.3 m from the bottom of the reactor is packed with SiC.) |
| Feed | 98.65 wt % of 2,3-butanediol and earlier gas ($N_2$) |
| Processing conditions | Pressure: 0.2 bar |
| | Average temperature of catalyst bed: 300 to 350° C. |
| | WHSV(*1): 0.5 to 2 $h^{-1}$ |
| Heating type | Outer wall of the reactor is electrically heated |
| | (the same value as the temperature of the feed of the reactor is set) |

(*1) Weight Hourly Space Velocity (WHSV)
WHSV [1/hr] = rate of packing of feed except for $N_2$ [g/hr]/catalyst weight [g]

While the main operating factors, namely the inlet temperature of the reactor and the WHSV, were changed, dehydration was performed. The results are shown in Table 3 below.

TABLE 3

| | Run 1 | Run 2 | Run 3 | Run 4 | Run 5 | Run 6 |
|---|---|---|---|---|---|---|
| Operating Conditions | | | | | | |
| Inlet temperature [° C.] | 300 | 310 | 320 | 330 | 340 | 350 |
| Outlet temperature [° C.] | 299 | 308 | 317 | 328 | 340 | 350 |
| WHSV [/hr] | 0.5 | 0.48 | 0.51 | 0.5 | 0.52 | 0.48 |
| Pressure [bar] | 0.22 | 0.21 | 0.2 | 0.2 | 0.21 | 0.2 |
| N2 [g/hr] | 393 | 391 | 390 | 392 | 396 | 393 |
| Reactor Performance (wt %) | | | | | | |
| 2,3-BDO Conversion | 22.15 | 46.76 | 88.55 | 99.99 | 100.00 | 100.00 |
| 1,3-Butadiene | 7.31 | 10.72 | 14.80 | 29.63 | 32.40 | 33.80 |
| 2-Methyl Propanal | 8.45 | 7.48 | 6.59 | 5.81 | 5.18 | 4.64 |
| 2-Butanone (MEK) | 35.40 | 34.75 | 33.52 | 32.00 | 30.57 | 29.23 |
| 3-Buten-2-ol | 21.76 | 21.21 | 18.95 | 1.62 | 0.00 | 0.00 |
| WATER | 27.07 | 25.82 | 26.09 | 30.76 | 31.56 | 31.65 |
| Unknown | 0.012 | 0.020 | 0.048 | 0.175 | 0.302 | 0.679 |
| Sum | 100 | 100 | 100 | 100 | 100 | 100 |

| | Run 7 | Run 8 | Run 9 | Run 10 | Run 11 | Run 12 |
|---|---|---|---|---|---|---|
| Operating Conditions | | | | | | |
| Inlet temperature [° C.] | 302 | 309 | 320 | 332 | 338 | 351 |
| Outlet temperature [° C.] | 299 | 308 | 316 | 324 | 334 | 349 |
| WHSV [/hr] | 1.01 | 1.03 | 0.99 | 0.98 | 1.02 | 1 |
| Pressure [bar] | 0.19 | 0.2 | 0.21 | 0.21 | 0.21 | 0.19 |
| N2 [g/hr] | 392 | 390 | 392 | 393 | 393 | 395 |
| Reactor Performance (wt %) | | | | | | |
| 2,3-BDO Conversion | 11.49 | 24.41 | 47.31 | 81.37 | 99.93 | 100.00 |
| 1,3-Butadiene | 6.70 | 10.03 | 13.67 | 17.62 | 28.59 | 33.42 |
| 2-Methyl Propanal | 8.02 | 7.29 | 6.51 | 5.84 | 5.26 | 4.78 |
| 2-Butanone (MEK) | 33.59 | 33.87 | 33.09 | 31.99 | 30.76 | 29.59 |
| 3-Buten-2-ol | 20.96 | 21.23 | 19.94 | 17.37 | 4.79 | 0.00 |
| WATER | 30.72 | 27.57 | 26.78 | 27.15 | 30.56 | 32.10 |
| Unknown | 0.009 | 0.010 | 0.016 | 0.028 | 0.031 | 0.102 |
| Sum | 100 | 100 | 100 | 100 | 100 | 100 |

| | Run 13 | Run 14 | Run 15 | Run 16 | Run 17 | Run 18 |
|---|---|---|---|---|---|---|
| Operating Conditions | | | | | | |
| Inlet temperature [° C.] | 302 | 311 | 320 | 329 | 343 | 352 |
| Outlet temperature [° C.] | 299 | 308 | 316 | 323 | 329 | 335 |
| WHSV [/hr] | 2.02 | 2.01 | 2.02 | 1.98 | 1.99 | 2.04 |
| Pressure [bar] | 0.19 | 0.2 | 0.19 | 0.2 | 0.2 | 0.22 |
| N2 [g/hr] | 391 | 393 | 394 | 392 | 395 | 390 |
| Reactor Performance (wt %) | | | | | | |
| 2,3-BDO Conversion | 5.95 | 12.70 | 24.84 | 43.49 | 67.92 | 93.84 |
| 1,3-Butadiene | 5.90 | 9.24 | 12.84 | 16.50 | 20.10 | 24.37 |
| 2-Methyl Propanal | 7.29 | 6.95 | 6.34 | 5.74 | 5.25 | 4.84 |
| 2-Butanone (MEK) | 30.56 | 32.28 | 32.25 | 31.52 | 30.62 | 29.74 |

TABLE 3-continued

| | | | | | | |
|---|---|---|---|---|---|---|
| 3-Buten-2-ol | 19.33 | 20.67 | 20.13 | 18.32 | 15.77 | 11.79 |
| WATER | 36.90 | 30.84 | 28.43 | 27.91 | 28.23 | 29.18 |
| Unknown | 0.004 | 0.007 | 0.010 | 0.017 | 0.032 | 0.075 |
| Sum | 100 | 100 | 100 | 100 | 100 | 100 |

The conversion of 2,3-BDO and the selectivity of a product (j) were calculated using the following equations.

$$\text{Conversion} = (F_{in,2,3\text{-}BDO} - F_{out,2,3\text{-}BDO})/F_{in,2,3\text{-}BDO})/F_{in,2,3\text{-}BDO}*100$$

$$\text{Selectivity} = F_{out,j}/(F_{out} - F_{out,2,3\text{-}BDO} - F_{out,N2})*100$$

Here, F is a mass flow rate.

The temperature had a great influence on the selectivity of 1,3-butadiene and 3-buten-2-ol (3B2OL) but had no significant effect on the selectivity of methyl ethyl ketone (MEK) and 2-methyl propanal. At temperatures of 320° C. or more, 1,3-butadiene selectivity was increased but MEK selectivity was slightly decreased. The amount of impurities was increased with an elevation in the temperature, and the extent of increase thereof became larger in the relatively high temperature range. Also, while the selectivity of 1,3-butadiene was increased, the amount of impurities was also increased, and the lower the WHSV, the longer the retention time in the reactor, thus increasing the conversion of 2,3-butanediol.

During the conversion of 2,3-butanediol into 1,3-butadiene and methyl ethyl ketone, the following four main reactions occur, as shown in Main Schemes 1 to 4 below.

$C_4H_{10}O_2(2,3\text{-BDO}) \rightarrow C_4H_8O(3\text{-Buten-2ol}) + H_2O$ [Main Scheme 1]

$C_4H_8O(3\text{-Buten-2ol}) \rightarrow C_4H_6(1,3\text{-BD}) + H_2O$ [Main Scheme 2]

$C_4H_{10}O_2(2,3\text{-BDO}) \rightarrow C_4H_8O(\text{MEK}) + H_2O$ [Main Scheme 3]

$C_4H_{10}O_2(2,3\text{-BDO}) \rightarrow C_4H_8O(2\text{MPA}) + H_2O$ [Main Scheme 4]

Based on the above data results, when WHSV is increased at the same temperature, the conversion of 2,3-butanediol is linearly decreased, from which the above main reactions are deemed to be close to zero-order reactions. Thus, the performance of the reactor is understood to be determined not by the reaction feed but by the temperature.

Based on the above data results, in order to maximally convert 2,3-butanediol and in order to maximally increase the selectivity of 1,3-butadiene and methyl ethyl ketone in a 2,3-butanediol dehydration reactor on a commercial scale, 2,3-butanediol is passed through a plurality of adiabatic reactors, which are connected in series. Here, controlling the inlet and outlet temperatures of each of the adiabatic reactors was found to be the most appropriate.

FIG. 1 schematically shows the process of preparing 1,3-butadiene and methyl ethyl ketone from 2,3-butanediol according to an embodiment.

With reference to FIG. 1, four adiabatic reactors R101A, R102A, R103A, R104A are connected in series, which is merely an example. The number of reactors may be less than or more than four. In the present disclosure, a group of adiabatic reactors that are connected in series is defined as a train, and two or more trains may be connected in parallel with each other. FIG. 1 illustrates two trains that are connected in parallel with each other.

In the present disclosure, a reaction unit configured such that the adiabatic reactors are connected in series is used. The product obtained from the upstream adiabatic reactor may be supplied into the downstream adiabatic reactor after controlling the temperature thereof. An adiabatic reactor is a reactor that undergoes no heat exchange with the outside. Changes in the temperature of the reaction fluid are caused by the reaction heat because heat exchange with the outside is blocked.

FIG. 1 schematically shows the process of preparing 1,3-butadiene and methyl ethyl ketone from 2,3-butanediol according to an embodiment.

As shown in FIG. 1, four adiabatic reactors R101A, R102A, R103A, R104A are connected in series, which is merely an example. The number of reactors may be less than or more than four. In the present disclosure, a group of adiabatic reactors that are connected in series is defined as a train, and two or more trains may be connected in parallel with each other. FIG. 1 illustrates two trains that are connected in parallel with each other. In an exemplary embodiment, only one train may operate, and in another embodiment, two or more trains may simultaneously operate.

The stream including 2,3-butanediol is introduced into the first adiabatic reactor among the plurality of adiabatic reactors that are connected in series. The feed stream including 2,3-butanediol may include a carrier gas, for example, nitrogen gas. The feed stream including 2,3-butanediol is supplied into the first adiabatic reactor at a temperature ranging from 200° C. to 400° C., particularly 300° C. to 380° C., and more particularly 330° C. to 365° C. If the temperature is lower than 200° C., 2,3-butanediol may be liquefied. On the other hand, if the temperature is higher than 400° C., autoignition may occur. The feed stream including 2,3-butanediol may be heated via heat exchange with the product stream from the final adiabatic reactors R104A, R104B using the heat exchanger E101. Also, the feed stream including 2,3-butanediol may be heated to a temperature ranging from 200° C. to 400° C. via the main heating furnace H101.

2,3-butanediol, introduced into the first adiabatic reactor R101A, is dehydrated and converted into 1,3-butadiene and methyl ethyl ketone, after which the product stream including 1,3-butadiene and methyl ethyl ketone is discharged from the first adiabatic reactor. The dehydration reaction is endothermic, and thus the product stream is discharged at a temperature lower than the temperature of the stream supplied into the reactor. The product stream may be discharged at a temperature lower by 10° C. to 150° C., 40° C. to 100° C., or 60° C. to 80° C. than the temperature of the supplied stream depending on the endothermicity of the reactor. The lowered temperature of the product stream is elevated to the same temperature as the temperature of the stream supplied into the reactor by means of assistant heating furnaces H102, H103, H104, and then the product stream may be supplied again into the downstream reactor.

The product stream including 1,3-butadiene and methyl ethyl ketone may contain unconverted 2,3-butanediol and byproducts.

The product stream is heated to a temperature of 200° C. to 470° C. by means of a heater such as the assistant heating furnace H102, and is then supplied into the second adiabatic reactors R102A, R102B. These procedures are repeated up to the final adiabatic reactors, after which the final product stream may be obtained. In an exemplary embodiment, the final adiabatic reactors may be second adiabatic reactors R102A, R102B, third adiabatic reactors R103A, R103B, or fourth adiabatic reactors R104A, R104B.

As such, when the total conversion of 2,3-butanediol reaches a desired value, namely 99.9%, and the molar concentration of the intermediate product 3B2OL is 0.1% or less, the product stream is not supplied into the downstream adiabatic reactor, but may be obtained as a final product stream.

In an embodiment, the pressure of the stream supplied into the adiabatic reactor may fall in the range of 0.1 kgf/cm² g to 6 kgf/cm² g, particularly 0.5 kgf/cm² g to 4 kgf/cm² g, and more particularly 1 kgf/cm² g to 3 kgf/cm² g. If the pressure thereof is less than 0.1 kgf/cm² g, the fluid has difficulty flowing. On the other hand, if the pressure thereof exceeds 6 kgf/cm² g, reaction performance may deteriorate.

In an embodiment, the WHSV of the stream including 2,3-butanediol introduced into the inlet of the adiabatic reactor and the product stream including 1,3-butadiene and methyl ethyl ketone may fall in the range of 0.1 hr$^{-1}$ to 4.8 hr$^{-1}$, particularly 0.3 hr$^{-1}$ to 3 hr$^{-1}$, and more particularly 0.5 hr$^{-1}$ to 1.5 hr$^{-1}$. If the WHSV thereof is less than 0.1 hr$^{-1}$, many side reactions may occur due to the high retention time. On the other hand, if the WHSV thereof exceeds 4.8 hr$^{-1}$, the reaction does not sufficiently occur due to the low retention time.

<Regeneration Process>

During the dehydration, coke accumulated on the catalyst may be removed through oxidative regeneration. Such oxidative regeneration functions to remove coke accumulated due to combustion during the dehydration of 2,3-butanediol in the adiabatic reactor. In an embodiment, oxidative regeneration of the amorphous calcium phosphate catalyst may be performed by passing the $O_2/N_2$ gas mixture once at a low pressure.

In an embodiment, when one of two or more trains is operating, the $O_2/N_2$ gas mixture is passed through the remaining train, which is not operating, thereby regenerating the catalyst.

In an embodiment, the $O_2/N_2$ gas mixture stream is passed through the reactor at a temperature of 400° C. to 600° C., and particularly about 500° C., under approximately atmospheric pressure for 5 to 7 hr, and particularly 6 hr. The $O_2/N_2$ mixture molar ratio may be 5/95 to 20/80, or 10/90 to 15/75. After the regeneration process, the adiabatic reactor may be cooled to about 365° C., after which the feed may be supplied again.

A better understanding of the present disclosure may be obtained through the following Examples, which are merely set forth to illustrate but are not to be construed as limiting the scope of the present disclosure.

Example 1

As a dehydration catalyst, an amorphous calcium phosphate-based catalyst (Ca/P molar ratio=1.2) was used, four adiabatic reactors were connected in series, and the dehydration of 2,3-butanediol was carried out under the conditions shown in Table 4 below. The inlet temperature of the reactor indicates the temperature of the stream introduced into the reactor. The reaction results are shown in Table 5 below.

TABLE 4

| Reactor | Reactor inlet pressure [kgf/cm²g] | WHSV [1/hr] | Reactor inlet temperature [° C.] | Reactor size Width [m] × length [m] |
|---|---|---|---|---|
| 1 | 2.2 | 0.983 | 365 | 5.0 × 2.2 |
| 2 | 1.85 | 0.972 | 365 | 5.0 × 2.2 |
| 3 | 1.5 | 0.978 | 365 | 5.0 × 2.2 |
| 4 | 1.21 | 0.958 | 365 | 2.4 × 7.5 |

Comparative Example 1

The dehydration of 2,3-butanediol was performed in the same manner as in Example 1, with the exception that the WHSV of the first adiabatic reactor was 4.91. The reaction results are shown in Table 5 below.

Each conversion was low, to a level of about 20%, from the first reactor to the third reactor due to the low retention time, and a conversion of 97.3% was obtained after the final reactor for converting the unreacted feed. However, the production reaction of 1,3-BD did not efficiently progress due to the low retention time, thus exhibiting BD selectivity of 20.9%.

Comparative Example 2

The dehydration of 2,3-butanediol was performed in the same manner as in Example 1, with the exception that the fourth adiabatic reactor was not provided. The reaction results are shown in Table 5 below.

As is apparent from Table 5, while passing through the first to the third adiabatic reactors, the conversion of 2,3-butanediol (BDO) was 93.4%, but unconverted 3B2OL was not converted into butadiene (BD) while passing through the three reactors, and thus the butanediol selectivity was low, to the level of 17.8%. In order to convert the feed, which is not converted due to the inactivation of the catalyst, into the final products 1,3-butadiene and MEK, the fourth adiabatic reactor needs to be designed to be longer than the first to the third adiabatic reactors.

TABLE 5

| | Unit | Example 1 | Comp. Example 1 | Comp. Example 2 |
|---|---|---|---|---|
| 1$^{st}$ Reactor outlet temperature | [° C.] | 293 | 308 | 293 |
| 2$^{nd}$ Reactor outlet temperature | [° C.] | 293 | 308 | 293 |
| 3$^{rd}$ Reactor outlet temperature | [° C.] | 294 | 309 | 294 |
| 4$^{th}$ Reactor outlet temperature | [° C.] | 297 | 293 | — |
| BDO total conversation | % | 100 | 97.3 | 93.4 |
| 1$^{st}$ Reactor BDO conversation | % | 32.3 | 23.1 | 32.3 |
| 2$^{nd}$ Reactor BDO conversation | % | 31.2 | 22.4 | 31.2 |
| 3$^{rd}$ Reactor BDO conversation | % | 29.9 | 21.8 | 39.9 |
| 4$^{th}$ Reactor BDO conversation | % | 6.6 | 30.1 | — |
| BD Selectivity | % | 30.3 | 20.9 | 17.8 |
| MEK Selectivity | % | 32.3 | 31.1 | 32.5 |
| 2MPA Selectivity | % | 6.2 | 5.6 | 6.3 |
| 3B2OL Selectivity | % | 0.02 | 14.3 | 16.3 |
| Average BD yield | % | 30 | 21.0 | 16.7 |

Although the embodiments of the present disclosure have been disclosed for illustrative purposes, those skilled in the art will appreciate that various modifications, additions and substitutions are possible, without departing from the scope and spirit of the disclosure as disclosed in the accompanying claims.

Accordingly, simple modifications or variations of the present disclosure fall within the scope of the present disclosure as defined in the accompanying claims.

What is claimed is:

1. A method of preparing 1,3-butadiene and methyl ethyl ketone from 2,3-butanediol, comprising:

a) providing a plurality of adiabatic reactors, which include a catalyst bed for dehydrating 2,3-butanediol, without a heat transfer medium, and are connected in series;

b) introducing a stream including 2,3-butanediol at a temperature ranging from 200° C. to 400° C. into a first adiabatic reactor among the plurality of adiabatic reactors;

c) dehydrating the 2,3-butanediol so as to be converted into 1,3-butadiene and methyl ethyl ketone and discharging a product stream including 1,3-butadiene and methyl ethyl ketone;

d) heating the discharged product stream to 200° C. to 400° C.; and e) introducing the heated product stream into a second adiabatic reactor so that 2,3-butanediol is further dehydrated and converted into 1,3-butadiene and methyl ethyl ketone and then discharging the product stream including 1,3-butadiene and methyl ethyl ketone.

2. The method of claim 1, further comprising f) heating the product stream, discharged from the second adiabatic reactor, to 200° C. to 400° C. and sequentially introducing the product stream into a subsequent adiabatic reactor.

3. The method of claim 2, wherein, when a conversion of 2,3-butanediol in the product stream is 99.9% or more, the product stream is not supplied into the subsequent adiabatic reactor but is obtained as a final product stream.

4. The method of claim 2, wherein, when a molar concentration of 3-buten-2-ol (3B2OL) in the product stream is 0.1% or less, the product stream is not supplied into the subsequent adiabatic reactor but is obtained as a final product stream.

5. The method of claim 1, wherein the heating the discharged product stream in d) is performed in a manner in which a temperature of the product stream is increased by 10° C. to 150° C.

6. The method of claim 1, wherein the catalyst for dehydrating is an amorphous calcium phosphate-based catalyst.

7. The method of claim 5, wherein a Ca/P molar ratio of the amorphous calcium phosphate-based catalyst ranges from 1.20 to 1.67.

8. The method of claim 1, wherein a pressure of the stream introduced into the adiabatic reactor ranges from 0.1 kgf/cm$^2$ g to 6 kgf/cm$^2$ g.

9. The method of claim 1, wherein a weight hourly space velocity of the stream introduced into the adiabatic reactor ranges from 0.1 hr$^{-1}$ to 4.8 hr$^{-1}$.

* * * * *